Figure 1:
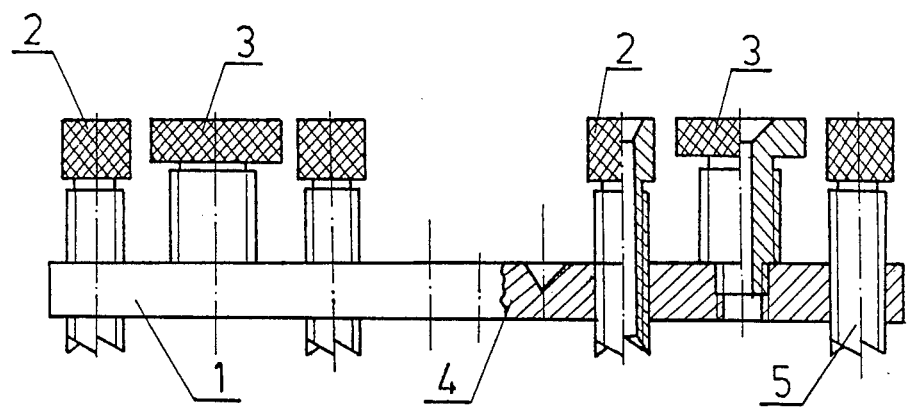

United States Patent [19]

Kara et al.

[11] Patent Number: 4,788,970
[45] Date of Patent: Dec. 6, 1988

[54] DRILL SETTING GUIDE FOR DRILLING HOLES IN BONES

[75] Inventors: Włodzimierz Kara, Dąbrowa Górnicza; Robert Granowski; Witold Ramotowski, both of Warsaw; Aleksander Tuziemski, Sosnowiec; Jerzy Cieplak, Dąbrowa Górnicza; Kazimierz Pilawski, Warsaw, all of Poland

[73] Assignee: Huta Baildon, Katowice, Poland

[21] Appl. No.: 33,410

[22] Filed: Apr. 1, 1987

[30] Foreign Application Priority Data

| Apr. 1, 1986 [PL] | Poland | 76944[U] |
| Apr. 1, 1986 [PL] | Poland | 258787 |
| Apr. 1, 1986 [PL] | Poland | 76943[U] |
| Apr. 1, 1986 [PL] | Poland | 258786 |
| Dec. 19, 1986 [PL] | Poland | 263197 |

[51] Int. Cl.⁴ .................................. A61M 37/00
[52] U.S. Cl. ........................ 128/92 ND; 128/92 R; 128/92 V
[58] Field of Search ............. 128/92 VD, 92 V, 92 R

[56] References Cited

U.S. PATENT DOCUMENTS

| 4,360,012 | 11/1982 | McHarrie et al. | 128/92 VD |
| 4,364,318 | 12/1982 | Sher et al. | 128/92 VD |
| 4,502,475 | 3/1985 | Weigle et al. | 128/92 VD |
| 4,570,624 | 2/1986 | Wu | 128/92 VD |
| 4,599,999 | 7/1986 | Klave | 128/92 VD |

Primary Examiner—C. Fred Rosenbaum
Assistant Examiner—Colleen Reilly
Attorney, Agent, or Firm—Ladas & Parry

[57] ABSTRACT

The subject of this present invention is a drill setting guide used for drilling holes in bones. The subject of this present invention is disclosed in an embodiment shown in FIG. 7 which shows a guide whose body consists of two round-sectioned parts as shown in a front half section.

Body 1 has tapped holes into which drill guide bushes 2 with lock nuts 6 placed above body 1 have been screwed. Further on, drill guide bushes 2 are provided with blades 5.

Body 1 consists of two parts slideably interconnected to each other by means of guides 10 and coaxially applied knurled nut 11 with a scale engraved thereon. At the ends of body 1 there is lock 12 for securing component 13 that extends body 1.

8 Claims, 6 Drawing Sheets

DRILL SETTING GUIDE FOR DRILLING HOLES IN BONES

The subject of this present invention is a drill setting guide for drilling holes in bones in the therapy of breaks by the plate anastomosis method. There is in the recent years an increasing tendency aimed in orthopedic surgery not only at connecting bone fragments, but also at their internal strong immobilisation enabling gypsum dressing to be dispensed with. This is a therapeutic method defined as the stable osteosynthesis. One of the methods of stable anastomosis involves connecting bone fractures with holed bone plates and bone screws.

Depending on the kind of fracture, the anastomosis involving the use of bone plates and screws can be performed as:

neutralising, without the pressure of fractures and with the application of protective plates;

pressed when the fragments compress each other.

During neutralising anastomosis, operative surgery is earried out by the method to be described below.

The holed plate to be used together with the screws is bent to the shape of the bone, is placed on the bone and is temporarily immobilised.

Next, holes are drilled in the bones.

Single guides in the form of a short bush with a handle are used for drilling holes in bones.

The lower part of the bush terminates in a conical end adapted to the hole in the bone plate. The guide is set over successive holes in the plate in such a way that the hole to be drilled with a drill introduced in the guide should be strictly aligned with the hole of the plate and the hole axis should also be perpendicular to the bone. Subsequently, the holes made in the bone are tapped, and the bone screws are screwed in for securing the holed plate.

When using pressed anastomosis and the locating plate of the compression apparatus, the guide for the compression apparatus is used for fitting the locating plate.

The operative surgery with using the guide for the compression apparatus is performed in the manner described below.

The locating plate is matched to the shape of the bone. Next, it is placed on the bone and locked in place. Using a guide shaped as a bush, having a handle and fitted into the holes of the plates, holes are drilled in the bone to receive the bone screws. These holes are drilled on one side of the fracture gap. Bone screws are fitted into the drilled and tapped holes and thus the plate is secured on that side of the failure gap.

The pilot of the guide for the compression apparatus is pushed into the end hole on the side of the plate not secured to the bone. The pilot of the guide for the compression apparatus is connected by means of a plate to a simple drill bush which rests at a definite distance from the end of the plate on the bone on the other side of the fracture gap. A drill is fitted into the drill bush, a hole is drilled and next tapped for mounting the foot of the compression apparatus.

The compression apparatus is used for pressing that part of the bone which has not been connected to the plate to the fracture being locked. Next, further holes are drilled in the bone according to those made in the plate and, next, tapped, the bone screws are introduced and the compression apparatus.

Self-pressing plates are used for compression anastomosis. At one of its ends the self-pressing plates have round holes and taper compression holes at the other. For the purpose of securing the plate to a bone it is necessary to model it in such a way that it should fit to the shape of the broken bone. Next the plate is placed on the bone and, using a bush-shaped guide holes are drilled and tapped.

In addition to the above, an end of the locating plate having round holes is secured to the bone fragment on one side of the fracture gap by means of bone screws. After the end of the locating plate has been secured, the pressure end is secured on the other side of the fracture gap. With that end in view holes are drilled using a guide in the shape of a long bush terminating in teeth ensuring a reliable rest of the guide against the bone.

The guide is then fitted into a successive plate hole and, next, holes are drilled through them and then, tapped. Bone screws are fitted to cause the bone fragments to be pressed to each other. The drill guides used until now for drilling holes in bones for the purpose of securing the plates with bone screws are used for drilling single holes. The construction of the guides in the form of a single line does not ensure that holes with their axes perpendicular to the bone surface will be drilled. Such guides do not allow an optimum force for pressing the bone fragments to be obtained.

The quality of the anastomosis largely depends on the optimum compression of bone fragments. Too high a compression that can be obtained with the application of the compression apparatus leads to the ends of the bone fragments to be crushed and causes their edge necrosis, thereby preventing their correct healing. In addition, too weak a compression of the bone fragments causes static and dynamic forces to be transmitted by the plate only, which can cause it to be broken.

Further work on improving the method of the therapy of fractures with plate anastomosis has led to the development of the design of a guide comprising some drill guiding components. That guide consisted of two arms provided with drill guiding holes. These arms were mounted at the ends of telescopic connector. The ends of the telescopic connector were connected on one side to the guide arms and on the other side to a bolt with a scale. Bosses were provided in these arms round the drill guiding holes.

The spacing of the arms is set by means of the bolt with a scale in such a manner that the axes of the drill guiding holes coincide with those of the holes of the locating plate. The so prepared guide is applied to a bone, and it rests on it with its bosses. Next, holes are drilled in the hole by introducing a drill into a successive hole in the guide. After holes have been drilled in the bone, they are tapped, the guide is removed, a suitably profiled connecting plate is secured by means of bone screws that are screwed into the tapped holes.

The guide of such construction also showed many disadvantages.

Due to the rigid construction of the arms the bosses do not adhere over its entire length once the guide has been applied to bone fragments due to various analomical bends of the bone. This causes the guide-drill system to be unstable when holes are being drilled, causing the guide to slide down.

In view of the low stability of the above-mentioned system it is not possible to prevent the axis of the hole being drilled from deviating in the plane perpendicular to the surface of the bone. Consequently, it is not possible to maintain an accurate spacing between the axes of consecutive holes.

The holes made in the way described above cause difficulties in the correct axial introduction and tightening of the screws and in the faultless anatomical resetting of bone fragments, and the magnitude of tightening torque applied highly varies. This leads to impaired bone accretion. Besides, the applicaton of the said guide tends to cause the arms to incline and the bolts connecting the arms to the telescopic connectors to lock.

The guides can be used only for one length of the plate and enable holes to be drilled at one hole spacing. During the surgical therapy they cover the field of operation and are not suitable for the anastomosis of fractures with a transversal gap which are very extended and have intermediate fractures.

In practice, three hole spacings are principally encountered, i.e. holes which enable the anastomosis of bone fragments without compression, with moderate compression and with heavy compression. The selection of compression depends on the kind of fracture. The research carried out in the field of the biomechanics of bone fracture anastomosis allowed a relation to be established between basic structure, fragment displacement and compression force.

For the purpose of attaining correct therapy by the method of the anastomosis of bone fragments with the connecting plate a new design of the drill guide has been developed for drilling holes in bones for introducing bone screws that secure the connecting plate.

The essence of the design as per this present invention involves a guide having a body with holes into which are introduced drill guide bushes provided at their bottom with blades and bushes used for securing clamps.

The drill guide bushes are provided with lock nuts disposed above the body. With the guide body having round section, the holes arranged in rows are laid out so that their spacing in a successive row corresponds to a different compression of bone fragments.

The guide body can also consist of two parts being slideably interconnected. When the guide body consists of two parts with flat shape they are slideably interconnected with dowels and a screw. On the other hand, when the body consists of two parts with round section, they are slideably connected by means of guides to a coaxially applied knurled nut with a scale engraved thereon.

Another connection of two body parts in the shape of bones is effected by a holder with a recess whose shape corresponds to that of the connecting plate secured to that holder. Along a longer side both the bones are provided with screws of a diameter corresponding to that of the hole in the connecting plate, these screws being introduced into the holes of the connecting plate. A mark is applied on the upper surface of the bone to indicate the compression force of bone fragments and compression direction. The fundamental advantages of the guide as per this present invention is the possibility of attaining an optimum compression of bone fragments as a function of their displacement. The drill guide bushes fitted into the holes tapped in the body can be set at different heights depending on the anatomical bends of the broken bone. This allows the guide to be rested on the bone along the entire body and the blades at the bottom of the drill guide bushes prevent sliding down during hole drilling.

For the guide to be reliably secured, the body has bushes for the clamps surrounding the bone and maintaining the guide at one position during the operation. The layout of the guide holes in one plane enables the drill to be perpendicularly applied to the bone through the drill guide bushes and holes to be drilled with one setting of the guide. Thanks to that, the spacing of successive holes can be accurately kept. The holes made in this way do not pose any difficulty in the correct axial introduction and tightening of the bone screws.

When the guide body has a round-sectioned shape with the holes spaced in the row relative to a given magnitude of the compression of bone fragments, it is possible using one guide to select an appropriate bone fragment compression value and to introduce the drill guide bushes into the correct row. On the other hand, when the body consists of two parts capable of being moved to and away from each other, the compression of bone fragments can be continuously regulated.

A sliding connection of the two parts of the body of the guide allows the inclination of the arms to be avoided as was otherwise the case with the guides employed until now. The sliding connection having the shape either of dowels and a screw or of guides with a coaxially applied knurled nut with an engraved scale allows the required compression of bone fragments to be planned.

The locks located at the ends of the body allow the guide to be extended by adding a component and a number of drill guide bushes corresponding to the length of the connecting plate.

The guide whose body consists of two bones secured to the connecting plate placed in a holder allows anastomosis to be performed on a transversal gap of a fracture and very extensive with an intermediate fracture. The bones are mounted in the holes of the connecting plate on bolts and are locked with typical nuts.

The individual bones can differ from one another by the axis spacing of bolts and holes for the drill bushes. Depending on the mutual shift of these axes, the fragments of the broken bone can be compressed with different forces. When the axes coincide one another, no compression occurs.

For the purpose of correctly matching the bone to the required compression, a number is engraved on the bone and it corresponds to the magnitude of compression in millimetres and an arrow which indicates the direction of the required compression.

The subject of this present invention is embodied in a drawing where

Figure 2:
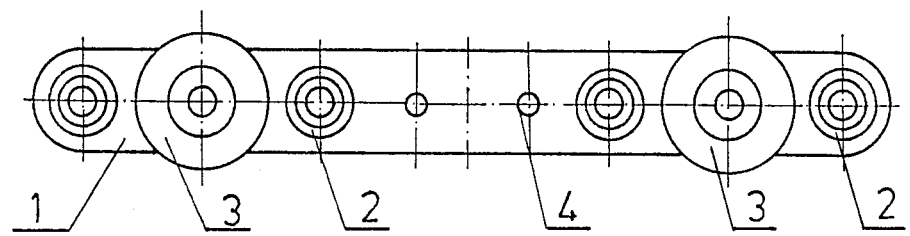
Figure 3:
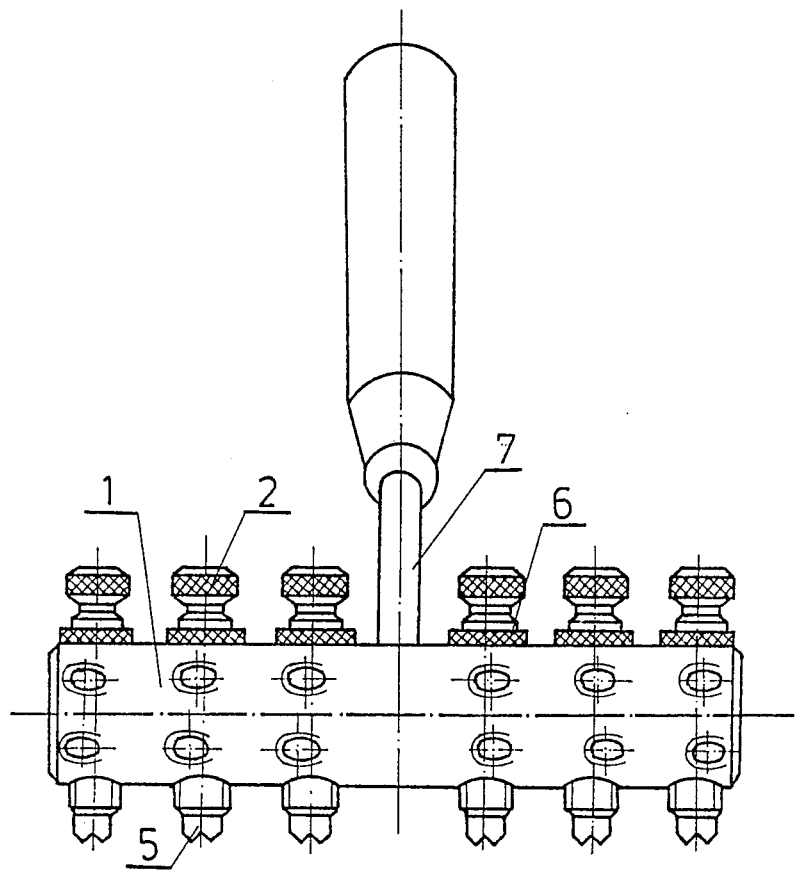
Figure 4:
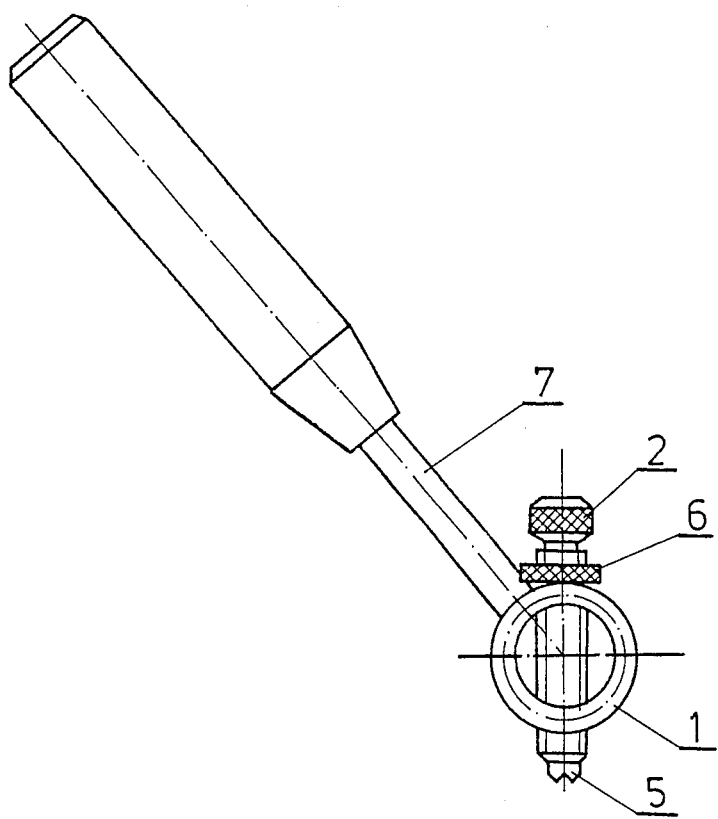
Figure 5:
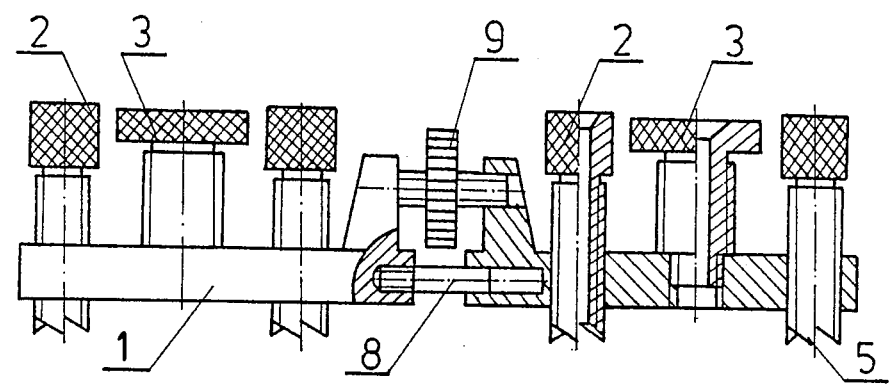
Figure 6:
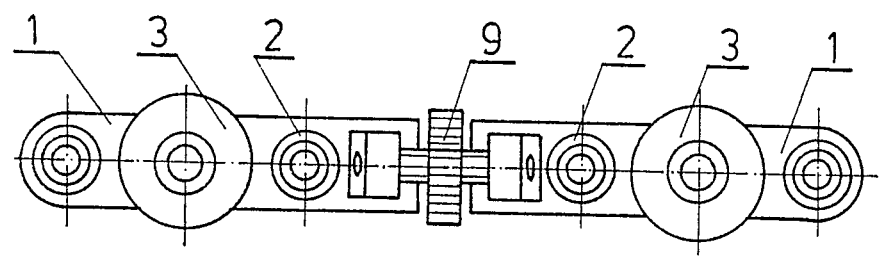
Figure 7:
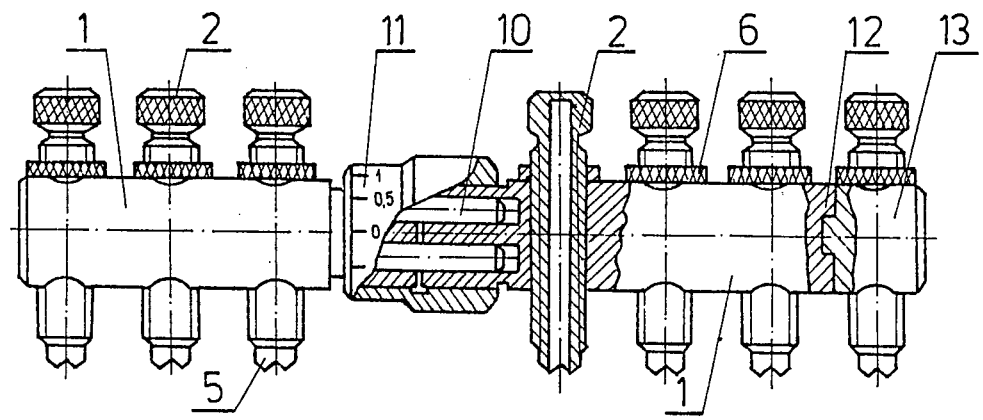
Figure 8:
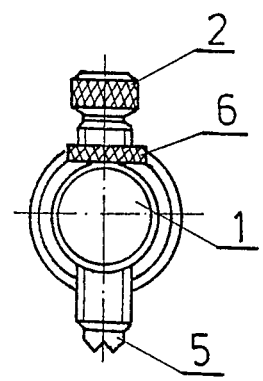
Figure 9:
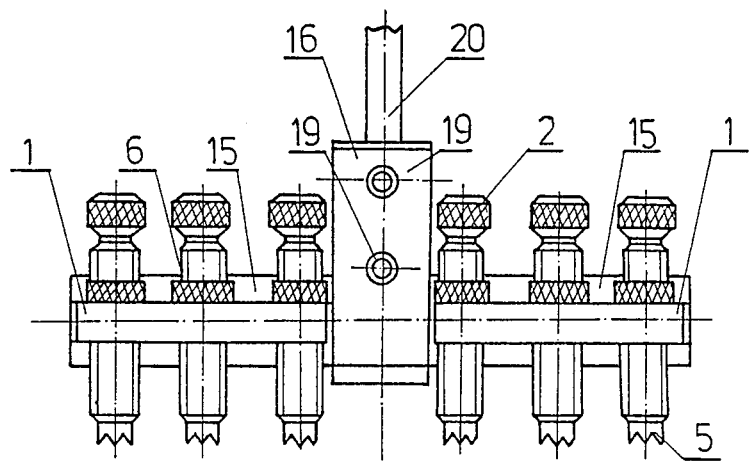
Figure 11:
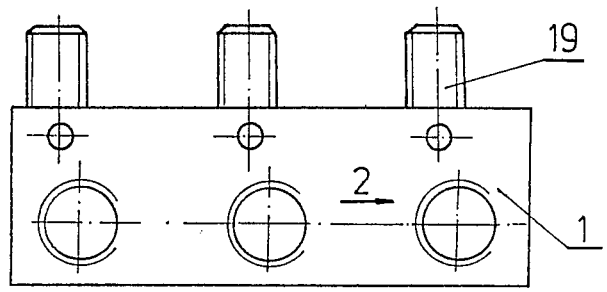
Figure 10:
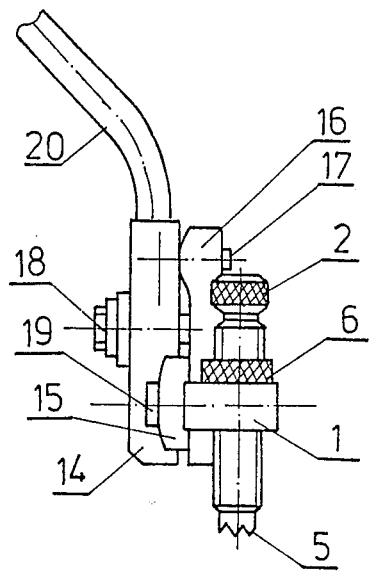

FIG. 1 shows a side half section of the guide whose body has the shape of a plate, FIG. 2 shows a top view of the same guide, FIG. 3 shows a front view of the guide whose body is round-sectioned, FIG. 4 shows a side view of the same guide, FIG. 5 a front half section of the guide whose body consists of two parts of the shape of plates, FIG. 6 shows the top view of the same guide, FIG. 7 shows a front half section of the guide whose body consists of two round-sectioned parts, FIG. 8 shows a side view of the same guide, FIG. 9 shows a front view of the guide whose body consists of two parts shaped like bones, FIG. 10 shows a side view of the same guide, and FIG. 11 shows a top view of the bone.

The essence of this present invention will be disclosed in the possible examples.

EXAMPLE 1

Body 1 shaped like a plate of the guide shown in FIGS. 1 and 2 has two tapped holes into which drill guide bushes 2 and clamp mounting bushes 3 have been screwed in. Drill guide bushes 2 and clamp mounting bushes 3 are symmetrically laid out on either side of body 1 relative to its transversial axis in such a way that clamp mounting bush 3 is between drill guide bushes 2.

Close to the transversal axis of symmetry of body 1 there are two recesses 4 used for fitting additional clamps that lock the guide in place. Drill guide bushes 2 have blades 5 in their bottom parts.

Prior to drilling holes in a bone drill guide bushes 2 are appropriately screwed in with allowance for the anatomical bends of the bone so that each of them rests with blade 5 on the bone. Next, the clamps are fitted around the bones to lock them in clamp mounting bushes 3 and recesses. With the guide being so mounted its body 1 is lifted about the fracture gap, thanks to which an orthopaedist can continuously control the drilling operation.

A drill is introduced through drill guide bushes 2 and successive holes are drilled in the bone. After having drilled the holes in the bone, the clamps and the guide are removed. At the same time bone fragments are prepared for receiving bone screws and for fitting the connecting plate.

EXAMPLE 2

Body 1 of the tubular section of the guide shown in FIGS. 3 and 4 has three rows of tapped holes appropriately spaced for anastomosis without compression, with medium compression and high compression. Drill guide bushes 2 having blades 5 in their bottom parts are screwed into the tapped holes. Drill guide bushes 2 are provided with lock nut 6 placed above body 1. Holder 7 is mounted in the middle part of body 1.

Drill guide bushes 2 are screwed into the tapped holes drilled in body 7 in such a manner that each drill guide bush 2 rests with its blade 5 on the bone. Screwed-in drill guide bushes 2 are locked with lock nuts 6 so that the drill should not cause drill guide bush 2 to shift when a hole is being drilled in a broken bone.

For the anastomosis of bone fragments without compression drill guide bushes 2 are screwed into a row of the holes whose axes coincide with those of the holes of the pressure plate. Holder 7 is used for keeping the guide in the required position.

EXAMPLE 3

Body 1 of the guide presented in FIGS. 5 and 6 consists of two parts shaped like plates interconnected with guiding dowels 8 and adjustment screw 9. Drill guide bushes 2 and clamp mounting bushes 3 are introduced into the holes drilled in body 1. The ends of drill guide bushes 2 are provided with blades 5.

Body 1 together with drill guide bushes 2 and clamp mounting bushes 3 is applied to a broken bone. Drill guide bushes 2 are screwed in in such a way that each of them rests with blade 5 on the bone. The spacing of both the parts of body 1 is adjusted with adjustment screw 9. Thanks to an appropriate shift of the axes of the holes of drill guide bushes 2 relative those of the connecting plate, medium compression of bone fragments is attained after the screws and connecting plate have been fitted.

The guide is secured to the bone by means of the clamps snapped in clamp mounting bushes 3. Next, the drill is introduced into successive drill guide bush 2 and a hole is drilled in the bone. After the operation has been completed both the clamp and the guide are removed.

EXAMPLE 4

Body 1 of the guide presented in FIGS. 7 and 8 consists of two round-sectioned parts interconnected by means of guides 10. The guide is coaxially adjusted with knurled nut 11 with the hole axis displacement value engraved thereon. Drill guide bushes 2 with lock nut 6 placed above body are introduced into the holes tapped in body 1. At an end of body 1 there is lock 12 connecting component 13 extending body 1 by a length corresponding to that of the connecting plate being applied.

When applying the guide, drill guide bushes 2 are matched to the anatomical bends of the bone and, next, they are locked in place with nuts 6. Using knurled nut 11 the guide is previously preset for attaining the anastomosis of bone fragments without compression. Due to the fracture requiring the application of a longer connecting plate, body 1 is extended with component 13 connected to body 1 via lock 12.

The guide prepared in the way described above may be used for drilling holes in a bone by introducing a drill into successive drill guide bushes 2.

EXAMPLE 5

Connecting plate 15 additionally secured with pressure plate 16 is placed in the recess of holder 14 of the guide presented in FIGS. 9, 10 and 11. Pressure plate 16 is connected to holder 14 with dowel 17 and bolt 18. Body 1 in the form 1 two blocks is secured to connecting plate on either sides of holder 14. The blocks of body 1 are secured to connecting plate in such a manner that bolts 19 placed at a side of the block of body 1 enter the holes of connecting plate 15 and typical nuts are screwed thereon. Drill guide bushes 2, complete with lock nuts 6 are introduced into the tapped holes made in the blocks of body 1.

Number two to indicate that the compression force of bone fragments is high and an arrow indicating its direction are applied to the top surface of the block of body 1. Holder 14 is connected to handle 20.

Connecting plate 15 should be placed in the recess of holder 1 and pressed by means of pressure plate 16 and bolt 18. The blocks of body 1 should be screwed to connecting plate 15 so mounted by tightening the nuts on bolts 19 fitted into the holes of connecting plate 15. Using the block of body 1 marked zero, the axes of bolts 19 and of the holes to receive drill guide bushes 2 are made to coincide with one another, thanks to which the holes drilled in the bone and those of connecting plate 15 will also coincide with one another.

In the above-described situation, bone fragments will not be compressed. When the block of body 1 marked two is tightened in the similar way on the other side of body 1, the axes of bolts 19 will be shifted relative to the holes for drill guide bushes 2 by 2 mm, thereby shifting the holes drilled in the bone relative to the holes of connecting plate 15 also by 2 mm.

The direction of the compression of bone fragments is indicated by an arrow applied to the top surface of the block of body 1. When connecting plate 15 is screwed onto the screws mounted in the drilled holes, bone fragments will tend to shift by 2 mm and a high compression force will be developed between those bone fragments during the anastomosis.

We claim:

1. A drill setting guide used for drilling holes in a bone to which an associated bone fastening plate can be secured, comprising a body having a set of bushings, said bushings being provided with suitable blade edges in the portions which are adapted to contact the bone, the improvements which are characterized in that the drill bushings are mounted in the guide body and in that there are securing nuts threaded on said bushings in such a way that said nuts are situated close to the guide body.

2. A guide according to claim 1, wherein the guide body has a set of tapped holes into which additional bushings are securely fastened to enable securing clamping means thereto.

3. A guide according to claim 1, wherein the guide body in cross-section has a circular shape and is provided with sets of tapped holes situated in axial rows and arranged in such a way that their spacing in each row provides a different degree of compression of bone fragments upon assembly with said associated bone fastening plate.

4. A guide according to claim 1, wherein the guide body comprises two parts of a planar shape slidably connected in a coplanar relationship by means of coaxial pin means and an adjustable screw to enable different degrees of compression of bone upon assembly with said associated plate.

5. A guide according to claim 1, wherein the guide body comprises two coaxial parts having a circular shape in cross-section connected slidably by means of parallel guide means with a coaxial knurled adjustable nut having a scale indicating lateral displacement of holes to be drilled, said guide body being provided with locking means at each end of the body to enable the addition of extension components to said body.

6. A guide according to claim 1, wherein the guide body comprises two coplanar parts having in cross-section the shape of prisms and slidably mounted in a connecting plate accommodated in a holder having a recess corresponding to the shape of the said connecting plate to enable axial adjustment of the guide holes to enable different degrees of bone compression upon assembly with an associated plate.

7. A guide according to claim 6, wherein the prism shaped guide body is provided with suitable screws arranged along the longer side with diameters corresponding to those of the holes in the connecting plate.

8. A guide according to claim 6, wherein on the top surface of the guide body there is a mark indicating the desired compression setting for the bone fragments and the direction of application of the selected compressive force.

* * * * *

UNITED STATES PATENT AND TRADEMARK OFFICE
CERTIFICATE OF CORRECTION

PATENT NO. : 4,788,970
DATED : December 6, 1988
INVENTOR(S) : Wlodzimierz KARAS et al It is certified that error appears in the above—identified patent and that said Letters Patent is hereby corrected as shown below:

Title page, paragraph [19]:    Cancel "Kara et al." and insert --Karas et al.--.

Title page, paragraph [75]:    Cancel "Kara" and insert --Karas--.

Signed and Sealed this

Fifteenth Day of August, 1989

*Attest:*

DONALD J. QUIGG

*Attesting Officer*      *Commissioner of Patents and Trademarks*